United States Patent
Dencek

(10) Patent No.: US 11,109,651 B2
(45) Date of Patent: Sep. 7, 2021

(54) TECHNICIAN'S CORD POSITIONER

(71) Applicant: Debra M Dencek, Cave Creek, AZ (US)

(72) Inventor: Debra M Dencek, Cave Creek, AZ (US)

( * ) Notice: Subject to any disclaimer, the term of this patent is extended or adjusted under 35 U.S.C. 154(b) by 2 days.

(21) Appl. No.: 16/200,626

(22) Filed: Nov. 26, 2018

(65) Prior Publication Data

US 2019/0380457 A1    Dec. 19, 2019

Related U.S. Application Data

(63) Continuation-in-part of application No. 15/823,544, filed on Nov. 27, 2017, which is a continuation-in-part of application No. 29/605,921, filed on May 31, 2017, now Pat. No. Des. 859,237.

(60) Provisional application No. 62/590,480, filed on Nov. 24, 2017.

(51) Int. Cl.
  *A44C 15/00* (2006.01)
  *A44C 5/00* (2006.01)
  *A61C 1/08* (2006.01)

(52) U.S. Cl.
  CPC .......... *A44C 15/003* (2013.01); *A44C 5/0053* (2013.01); *A61C 1/08* (2013.01)

(58) Field of Classification Search
  CPC ............ A44C 5/007; A61B 90/53; A61C 3/04
  See application file for complete search history.

(56) References Cited

U.S. PATENT DOCUMENTS

| | | | |
|---|---|---|---|
| D39,960 S | 5/1909 | Mussillon | |
| 1,544,386 A | 6/1925 | Annette | |
| 2,373,328 A | 4/1945 | Morehouse | |
| 2,871,592 A | 2/1959 | Polzin | |
| D259,242 S | 5/1981 | Gilb | |
| 4,373,175 A * | 2/1983 | Mykkanen | A61N 1/14 361/212 |
| 4,680,668 A * | 7/1987 | Belkin | A61N 1/14 361/220 |
| 4,957,232 A | 9/1990 | Sprague | |
| 5,024,402 A | 6/1991 | Hamel | |
| D353,990 S | 1/1995 | Alfreds | |
| 5,517,838 A | 5/1996 | Moore | |
| 5,671,508 A * | 9/1997 | Murai | F16G 11/101 24/115 K |
| 5,802,676 A | 9/1998 | Tolan | |
| 5,845,374 A | 9/1998 | Briggs | |
| 6,085,393 A | 7/2000 | Tsui | |

(Continued)

*Primary Examiner* — Victor D Batson
*Assistant Examiner* — Matthew J Sullivan
(74) *Attorney, Agent, or Firm* — The Hill Law Firm, PLC; Scott A. Hill

(57) ABSTRACT

Positioning a cord of a corded instrument is accomplished by securing a wearable cord positioner around a wrist or arm of a technician, and then attaching a cord positioner attachment to the cord positioner for cords that are larger or smaller than the cord positioner is designed to accommodate. Multiple cord positioner attachments may be used with the same cord positioner, and the cord positioner attachments may be left attached to a cord permanently. Once a technician is done performing a task, the cord positioner attachment can simply be slipped off of the cord positioner attached to the technician and left with the cord so that it is never misplaced.

5 Claims, 3 Drawing Sheets

(56) References Cited

U.S. PATENT DOCUMENTS

| | | |
|---|---|---|
| 6,092,444 A | 7/2000 | Hsiao |
| 6,131,200 A | 10/2000 | McNamara |
| 6,140,929 A * | 10/2000 | Gannon ............... A61N 1/14 |
| | | 324/510 |
| 6,279,804 B1 | 8/2001 | Gregg |
| 6,467,132 B1 | 10/2002 | Robley |
| 6,490,767 B2 | 12/2002 | Haiduk |
| 6,523,229 B2 | 2/2003 | Severson |
| 6,581,885 B2 | 6/2003 | Polad |
| 6,676,674 B1 | 1/2004 | Dudai |
| 6,701,580 B1 | 3/2004 | Bandyopadhyay |
| 6,763,554 B1 | 7/2004 | Torrey |
| D495,972 S | 9/2004 | Petingill |
| D505,785 S | 6/2005 | Woody |
| D511,450 S | 11/2005 | Seth |
| 7,039,958 B2 | 8/2006 | Henricksen |
| 7,096,544 B2 | 8/2006 | Lusardi |
| D543,833 S | 6/2007 | Folk |
| 7,252,450 B2 | 8/2007 | Aguirre et al. |
| 7,356,888 B2 | 4/2008 | Chao |
| 7,624,480 B2 | 12/2009 | Coronel |
| 7,731,069 B2 | 6/2010 | Lopreiato |
| D652,756 S | 1/2012 | Lans |
| D660,740 S | 5/2012 | Cullen |
| D662,087 S | 6/2012 | Peller |
| D666,076 S | 8/2012 | Muratore |
| D667,043 S | 9/2012 | Couch, III |
| D675,123 S | 1/2013 | Nunez |
| 8,413,306 B2 | 4/2013 | Gallant |
| 8,458,864 B1 | 6/2013 | Patton |
| D693,992 S | 11/2013 | Dinunzio |
| D712,295 S | 9/2014 | Ennis |
| D729,045 S | 5/2015 | Cavenaugh |
| D732,933 S | 6/2015 | Jansen |
| D733,525 S | 7/2015 | Petzl |
| D740,106 S | 10/2015 | Cooper |
| 9,340,341 B2 | 5/2016 | Farrell |
| 9,550,550 B1 | 1/2017 | Housman |
| D794,490 S | 8/2017 | Lindgren |
| D811,859 S | 3/2018 | Orser |
| D813,016 S | 3/2018 | Deneau |
| 2001/0013277 A1 | 8/2001 | Galkiewicz |
| 2002/0020045 A1 * | 2/2002 | Nasu ................ A45F 5/02 |
| | | 24/546 |
| 2003/0110596 A1 | 6/2003 | Graham |
| 2003/0167605 A1 | 9/2003 | Schultz |
| 2003/0189806 A1 * | 10/2003 | Antila .............. A61N 1/14 |
| | | 361/220 |
| 2004/0003487 A1 | 1/2004 | Reiter |
| 2004/0167456 A1 | 8/2004 | Kingsford |
| 2005/0251967 A1 | 11/2005 | McNeill |
| 2006/0032032 A1 | 2/2006 | Cheng |
| 2009/0106948 A1 | 4/2009 | Lopez |
| 2009/0109593 A1 * | 4/2009 | Dela Pena ........... H05F 3/02 |
| | | 361/220 |
| 2010/0115732 A1 * | 5/2010 | Honeycutt ......... H04R 5/0335 |
| | | 24/3.3 |
| 2011/0010894 A1 * | 1/2011 | Honeycutt ............ A45F 5/02 |
| | | 24/3.1 |
| 2012/0018250 A1 | 1/2012 | Smith |
| 2013/0334385 A1 | 12/2013 | Steck |
| 2014/0182087 A1 | 7/2014 | St Jean |
| 2014/0262864 A1 | 9/2014 | Rothbaum |
| 2017/0246632 A1 | 8/2017 | Slepian |

\* cited by examiner

02 Cord positioner
10 Band (Strap, bracelet)
12 Loop-end
14 Loop
16 Adjustment holes
18 Connector end
20 Snap connector
22 Rivet
24 Body
26 Side
28 Raised portion
30 Base
32 Opening
34 Cord-holding portion
36 Relief
38 Channel
40 Buttress 50 attachment
52 attachment body
54 passage
60 attachment channel
62 attachment opening
64 attachment shoulder
66 attachment relief
68 attachment side
70 head
72 neck
76 alignment arm
78 guide 02 Cord positioner
10 Band (Strap, bracelet)
12 Loop-end
14 Loop
16 Adjustment holes
18 Connector end
20 Snap connector
22 Rivet
24 Body
26 Side
28 Raised portion
30 Base
32 Opening
34 Cord-holding portion
36 Relief
38 Channel
40 Buttress

TECHNICIAN'S CORD POSITIONER

BACKGROUND OF THE INVENTION

Dental instruments used to perform dental procedures are usually powered by a power source that is connected to the dental instrument using some sort of flexible cord. Air and electricity are common power sources.

While performing a procedure, the cord of a dental instrument frequently needs to be moved out of the way of a work area so that a dental technician can clearly see and perform their work. In order to maintain sanitary conditions between patients, most of the various instruments and tools used for a dental procedure are either thoroughly cleaned or discarded and replaced. Dental technicians try to avoid touching a cord before or after touching a patient's mouth, but it sometimes becomes necessary to position a cord away from a patient's face while trying to position a corded dental instrument.

SUMMARY OF THE INVENTION

The present invention is a cord positioner attachment used with a cord positioner that provides a sanitary method for a cord to be positioned by a dental technician's arm such that the technician can maneuver the cord without touching the cord with a hand. An easy to wipe down band with a cord holder portion is worn by the technician, preferably around a wrist of the technician. The cord positioner is designed to only work with a particular range of cord diameters, so larger or smaller cords would require separate cord positioners. Rather than having a technician wear multiple differently sized cord positioners, attachments are attached to larger or smaller cords such that a structure is provided that is ideally suited for a single cord positioner being worn by a technician. In a preferred embodiment, the cord positioner is molded as part of a flexible band so that there are few cracks or crevices that might be difficult to clean. The cord holder portion includes structure that helps a base resist bending and twisting a lot more than the rest of the band. Preferably, any hard-to-clean surfaces and crevices are designed into the removeable or disposable clip to minimize the time it takes to sanitize instruments and tools that are not disposable. Other types of technicians, such as tattoo artists, may find the present cord positioner attachment to be useful.

CALLOUTS USED IN FIGS. 1-12

Figure 1:
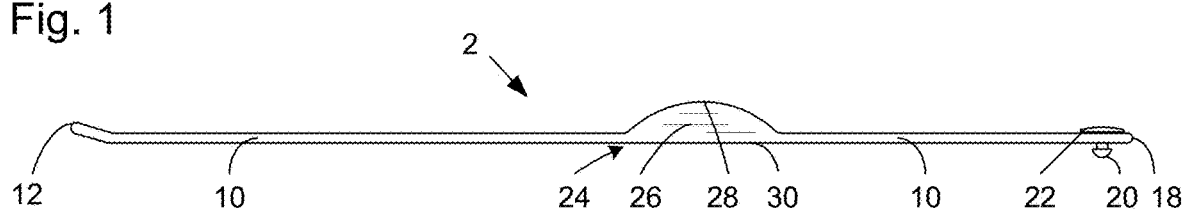
FIG. 1 is a side view of a cord positioner of the present invention.

02 Cord positioner
10 Band (Strap, bracelet)
12 Loop-end
14 Loop
16 Adjustment holes
18 Connector end
20 Snap connector
22 Rivet
24 Body
26 Side
28 Raised portion
30 Base
32 Opening
34 Cord-holding portion
36 Relief
38 Channel
40 Buttress
50 attachment
52 attachment body
54 passage
60 attachment channel
62 attachment opening
64 attachment shoulder
66 attachment relief
68 attachment side
70 head
72 neck
76 alignment arm
78 guide
80 technician

DETAILED DESCRIPTION OF THE INVENTION

Throughout this description, unless otherwise stated or shown, a cord positioner has two sides that are mirror images of each other when the apparatus is longitudinally bisected, so use of the plural for a single callout or feature is intended to describe both sides of the cord positioner in substantially the same way. Use of the same callout from drawing to drawing is intended to mean the same feature from a functional perspective even if features from drawing to drawing are not identical. The most preferred chord positioner, shown in FIGS. 1-5, is a cord positioner 2 characterized by a band 10 that has a centrally located body 24 that surrounds a channel 38. The body includes structures that allow a cord to be quickly and easily pressed into the channel such that the cord is attached to a technician's wrist or arm for easy manipulation of the cord without needing to grasp the chord with a free hand. The wearable band includes an aesthetic design that is comfortable to wear. The cord holder portion is preferably made from a flexible plastic material that is inexpensive. The cord holder portion is easy to manipulate so that it accepts a cord, and it is resilient such that it closes around the cord so that the cord is held in a desired alignment by the cord holder portion. In an alternate embodiment, the band and the cord holder portion are separate piece parts that fasten or clip together, and the cord holder portion is disposable or may be autoclaved.

The band can be a simple band or strap of material that wraps around a technician's arm, preferable near the wrist or elbow of the arm that is holding a corded instrument. A watch could be incorporated into the band, noting that it might be more difficult to clean. The preferred band is molded plastic, such as TPU, but the band can be substantially similar to any of the various watch bands or bracelets that offer comfort and support to a wearer. The band could also be an adhesively joined strip of Tyvek, similar to what is commonly used as a hospital identification band; or the band could be an adjustable vinyl or poly band, similar to what is commonly used as a medical alert bracelet. It is preferred that the band is somewhat flexible, yet the band should provide resistance to normal stresses that could unfasten the cord positioner. or it can be rigid. The term "strap" is meant to include any type of bracelet or wristwatch band type device, as well as any type of arm band.

The clip and strap are fastened to each other using a fastener, such as, but not limited to, a snap, clasp, hook, magnet or button. A snap or button would allow the clip to rotate relative to the strap. A detent can be incorporated into the fastener itself, such as into a button or snap, or a detent can be incorporated into the clip and strap such that when they are rotated relative to each other the detent disengages and engages until a desired position is selected. The clip and strap can be fastened to each other by incorporating a structure similar to a nylon plug, rivet or pin, with a preference that the hole for receiving the fastener is in the strap.

Figure 2:
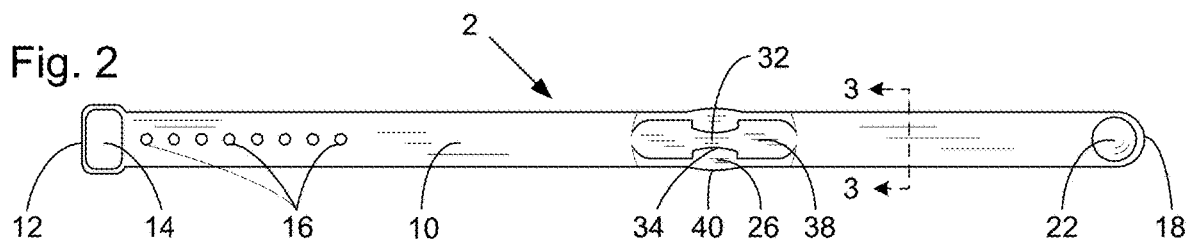
FIG. 2 is a plan view of the cord positioner of FIG. 1.

FIGS. 1 and 2 show a cord positioner 2 having a band 10 that straps around the wrist of a technician. The band has a loop-end 12 with a loop 14 and adjustable holes 16, similar to a common waist belt construction. At the opposite end, the band has a connector end 18 with a snap connector 20 and a rivet 22. The connector end is wrapped around a technician's wrist so that the connector end can be passed through the loop of the loop end until the rivet can be lined up with a desired adjustment hole and the band can be snapped together to secure it to the wrist of the technician. Other common ways of attaching a band around someone's wrist or arm may be employed, such as the various constructions of watch bands.

Somewhat centrally located on the band is the body 24 of the cord positioner 2. The body should be less flexible than the band, which may be accomplished by adding structure to the body, such as sides 26 that are raised relative to the otherwise flat band. The band preferably has a thickness of about 2 to 3 mm if it is to be attached around a wrist. The band shown in FIGS. 1-5, which is constructed to hold and position up to nominally sized 8 mm cords, is ideally about 13 mm wide, except that the loop end 12 and the body 24 should be wider. The overall length of the band, from connector end to loop end, is shown as being about 230 mm. The length of the band could be varied to accommodate wrist sizes that are smaller, or additional adjustment holes could be added to the band. For larger wrists sizes, a longer band would need to be constructed, such as 280 mm or longer.

The sides 26 of the body 24 are preferably their highest at raised portion 28, as shown in FIG. 1. The base 30 of the body 24 is fairly continuous with the band, but it is slightly wider to accommodate buttresses 40 on either side of the body. A cord positioner that accepts 8 mm cord is preferably about 9 mm high at the raised side portions 28. When considering that the base is a couple of millimeters thick, this means that it is intentional that an 8 mm cord will not fit inside channel 38 of the base without pushing apart opening 32.

Figure 3:
FIG. 3 is a cross-sectional view through line 3-3 of FIG. 2.
Figure 4:
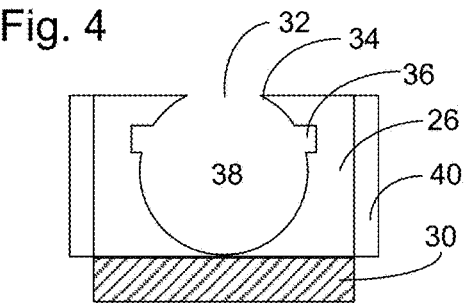
FIG. 4 is an enlarged view of FIG. 3.

Cord holder portions 34, most clearly seen in FIG. 4, which is an enlarged view of FIG. 3, which is a cross sectional view through line 3-3 of FIG. 2, are resilient and biased to pinch together at the opening 32. To allow for the opening to more easily expand when installing a cord into channel 38, reliefs 36 are provided, and buttresses 40 strengthen sides 26. Although the body could be constructed without buttresses or reliefs, these extra features seem to help with quality control when molding the cord positioner from a plastic material, such as TPU.

Installation of a cord into the channel is preferably accomplished when a user presses the cord of a corded instrument against the opening 32 in the body 24 of the cord positioner 2 until the cord-holder portions 34 spread apart enough to allow the cord to drop into channel 38. It is expected that a cord will deform a little bit during this process. Installation of the cord may be done when a technician is not wearing the cord positioner, but the preference is for a user to be wearing the cord positioner when pressing a cord into the channel. This means that the process should be relatively easy and capable of being performed with one free hand that grasps the cord and presses it into the opening 32. A technician may wiggle, roll and twist the cord against the cord holder portions a little to make this process easier. When the cord is installed into the cord positioner, most technicians will prefer that the instrument end of the cord is nearest the radial aspect of the technician's wrist, and a power supply end of the cord enters the cord positioner near the ulnar aspect of the technician's wrist. This is particularly true for corded instruments that are held like a writing instrument.

Figure 5:
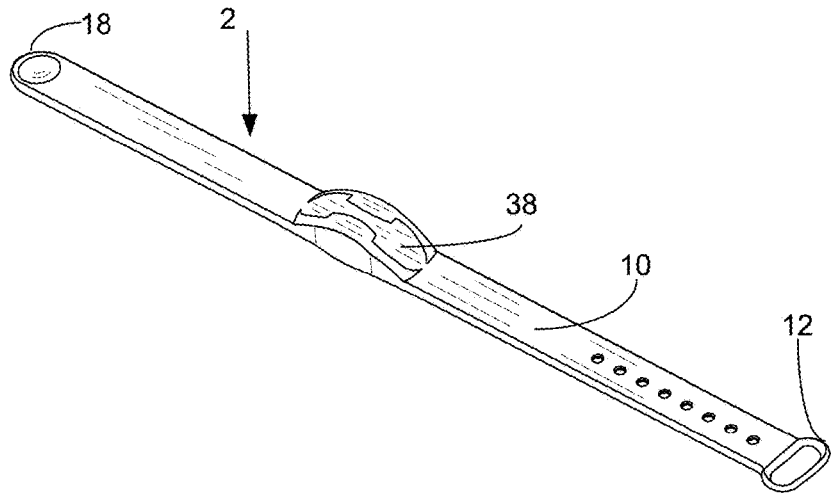
FIG. 5 is a perspective view of the cord positioner of FIGS. 1-4.

Smaller cords, such as 5 mm, may be used in a cord positioner designed for a larger cord, such as 8 mm. Because a smaller diameter cord is much lighter and usually more flexible, it is relatively secure within the channel 38, meaning that the cord holder portions aren't as likely to separate under the relatively small force exerted by any manipulations of a smaller cord when a technician maneuvers their wrist holding the cord positioner for the purpose of positioning their wrist to use the instrument without being annoyed or inconvenienced by the cord, or to manipulate the cord away from someone on whom a procedure is being performed. At it's narrowest, the opening is preferably about 2.5 mm wide from the cord holder portions on either side of the body. As shown in FIGS. 2 and 5, the opening is narrowest at a midpoint of the body because the width of the opening is tapered toward the midpoint. This allows a cord to be gradually less supported as it is farther from the midpoint to cause a more gradual bend of the cord when it is manipulated. A much smaller diameter cord than channel will allow the cord to slip back and forth through the channel. A sleeve may be added to a small diameter cord to reduce this slipping, if desired. Simply wrapping tape around a cord at a preferred length until it has a desired thickness is another method to reduce slipping.

Figure 6:
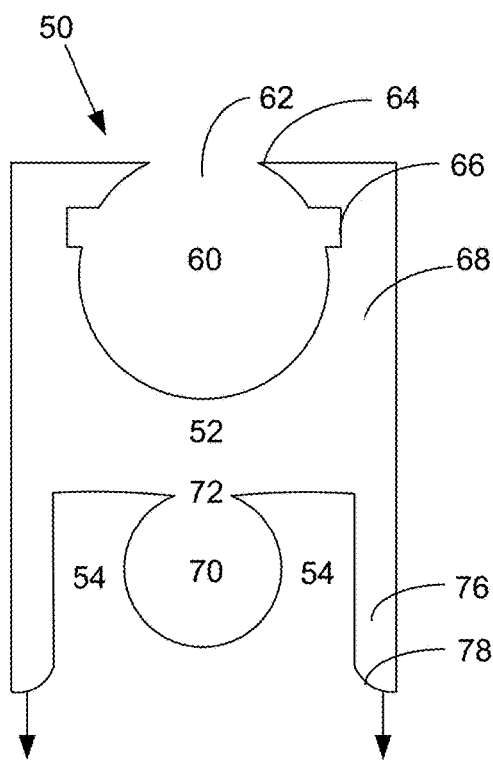
FIG. 6 is a front view of an attachment that attaches to the cord positioner of FIG. 4.
Figure 6:
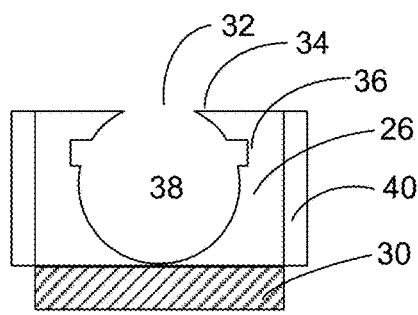
Figure 7:
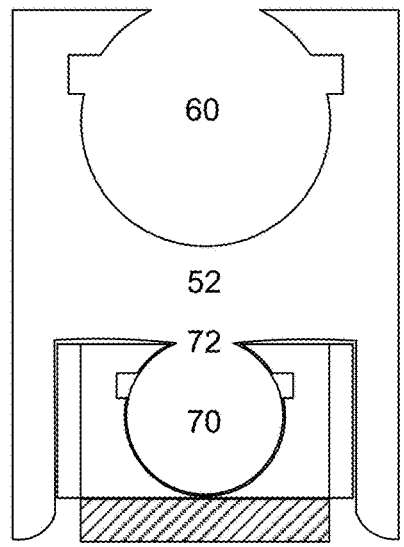
FIG. 7 is a front view of the attachment of FIG. 6 attached to the cord positioner of FIG. 4.

For larger cords, such as a 13 mm cord being used with an 8 mm cord positioner, cord positioner attachment 50 should be used because the larger cord will excessively deform the cord-holder portion 34 to the point that it is not able to adequately encompass the larger cord. As shown in FIGS. 6 and 7, the cord positioner attachment 50 has an attachment body 52. A head 70, which is preferably the same diameter as the channel 38 of the cord positioner 02, is connected to the attachment body 52 by a neck 72. Below the attachment body 52, on either side of the head 70, are alignment arm 76. Between the head 70 and alignment arm 76 is a passage 54. Above the attachment body 52 is a larger cord positioner substantially similar to the body 24 of the cord positioner 02 shown in FIGS. 1-5, but with the band cut off. The bottom piece part shown in FIG. 6 is substantially the same as the piece part shown in FIG. 4, meaning it could be the same preferred cord positioner as already described.

Above the attachment body 52 is an attachment channel 60, attachment opening 62, attachment shoulder 64, attachment relief 66 and attachment side 68, which are larger, but otherwise similar, to callouts 38, 32, 34, 36 and 26, respectively, shown in FIG. 4. Material choices and design considerations are also similar, so they are hereby incorporated for use with the cord positioner attachment 50. The plastic used may be more rigid than that used for the cord positioner 02 because it doesn't need to be comfortable or form fitting for a technician.

Because the cord positioner attachment 50 is larger, it may not be necessary to add a buttress to the attachment side 68. Also, the design aesthetics may be somewhat ignored because it is preferred that the cord positioner attachment 50 does not remain attached to the cord positioner 02 when not in use.

To use the cord positioner attachment 50, a technician manipulates it onto a larger cord in substantially the same manner as a cord is manipulated onto a cord positioner 02. Once the cord positioner attachment 50 is installed around a larger cord at a desired length of the larger cord, it is suggested that the cord positioner attachment 50 be left attached to the larger cord, even when not in use. Because the cord positioner attachment 50 is relatively large and chunky, it is not convenient to wear as an accessory when not being used, unlike the cord positioner 02.

To use the cord positioner attachment 50, a technician grasps it firmly, after it is attached to the larger cord, and slides the alignment arm 76 over the band 10 near the base 30, allowing the guide 78 to center the cord positioner attachment 50 over the cord positioner 02. Next, the technician slides the cord positioner attachment 50 lengthwise along the band 10 until the passage 54 directs the head 70 into the channel 38. The technician should fully insert the head 70 into the channel 38 so it is about centered inside the body 24. When properly aligned, the alignment arm 76 should slightly press against the buttress 40, and the cord holder portion 34 should nestle into the neck 72, as shown in FIG. 7. An other cord positioner attachment 50 may be interchanged and used with the same cord positioner 02. The other cord positioner attachment 50 may be for the same diameter of larger cord, or it may be a differently sized cord positioner attachment 50 for other size cords, even for smaller cords.

Figure 8:
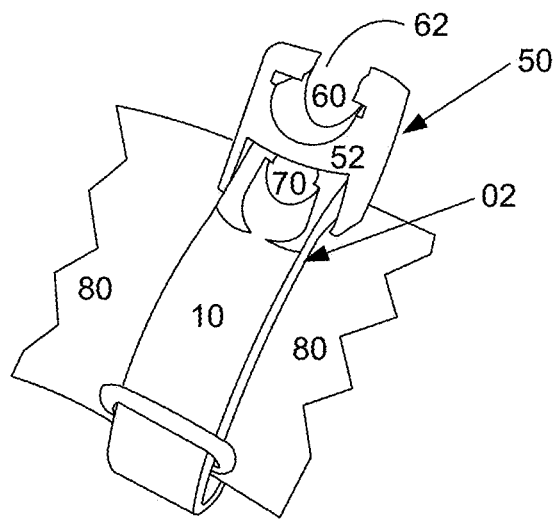
FIG. 8 is a perspective view of the cord positioner with a cord positioner attachment attached to the wrist of a technician.
Figure 9:
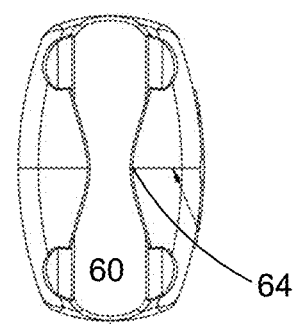
FIG. 9 is a plan view of an alternate cord positioner attachment of the present invention.
Figure 10:
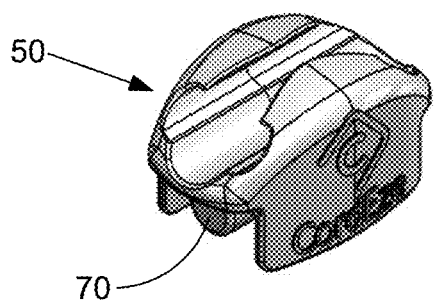
FIG. 10 is a perspective view of the cord positioner attachment of FIG. 9.
Figure 11:
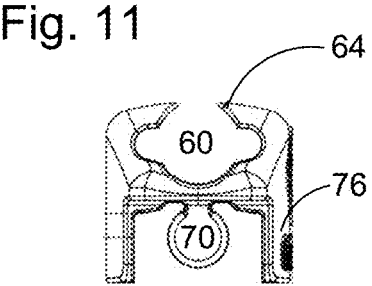
FIG. 11 is a front view of the cord positioner attachment of FIG. 9.
Figure 12:
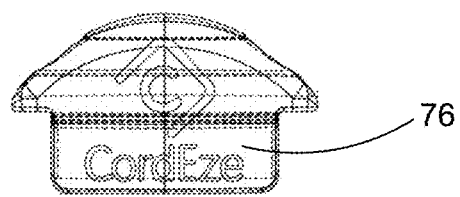
FIG. 12 is a side view of the cord positioner attachment of FIG. 9.

FIG. 8 shows a cord positioner attachment 50 according to the above description that has been attached to a cord positioner 02 that is being worn by a technician 80. FIGS. 9-12 are various views of an alternate cord positioner attachment 50 that is similar to the cord positioner shown in FIGS. 6-8, but the overall design has been smoothed out, including softened edges and rounded corners, to make it easier to clean the attachment. The cord positioner attachment of FIGS. 9-12 should work with the cord positioner 02 shown in FIGS. 1-5 in substantially the same way as the cord positioner attachment 50 of FIGS. 6-8.

In an alternative embodiment of the present apparatus, the larger cord is secured to the cord positioner attachment 50 by a means other than what is shown above the attachment body 52 in FIG. 6. Instead, a hook and loop strap is attached to the attachment body 52, the hook and loop strap being wrapped around the larger cord. This alternative embodiment is attached to the cord positioner in the same manner already described.

Yet another alternative embodiment of the present cord positioner attachment 50 is to have everything from the attachment body 52 down molded or otherwise permanently fixed to a larger cord. An attachment may be fixed to a cord using an adhesive strip, such as tape or other adhesive wrap. The attachment may alternatively be fixed to a cord using hook and loop straps, rubber straps, clips or other known ways to attach something to a cord. If an attachment is fixed to a cord by one of these other means, there may be no need for an attachment channel where a suitable alternative is provided.

In yet another alternative embodiment, the cord positioner includes a magnetic platform in place of the body, such as a flat steel platform that is magnetic; and the attachment 50 has a permanent magnet, such as a neodymium disc magnet or square magnet, in place of the head. An attachment with permanent magnet should be secured to a desired cord at a desired length, such as with an adhesive or Velcro wrap, before joining the cord positioner to the attachment. When brought into a desired alignment and proximity, the permanent magnet of the attachment will become magnetically joined to the cord positioner without needing to use a free hand to make the connection. Pulling the attachment away from the cord positioner will break the magnet bond when the tool is no longer being used by a technician. Preferably, the magnetic platform will include a relief in which the permanent magnet fits to prevent lateral movement of the attachment. A round magnet could include a detent structure to prevent rotation, but will otherwise fit in any orientation desired. A square magnet will fit in multiple orientations if the magnetic platform is also square. A magnetic platform could provide numerous orientations for a square magnet by being an octagram, or some other polygram formed using a set of squares that are just a little larger than a square magnet of an attachment.

While a preferred form of the invention has been shown and described, it will be realized that alterations and modifications may be made thereto without departing from the scope of the following claims.

What is claimed is:

1. A method for positioning a cord of a corded instrument, comprising the steps of:

securing a band of a cord positioner to a wrist of a technician, said band including a body;

attaching a first cord of a first corded instrument to the body;

positioning the first cord away from a procedure being performed by the technician by manipulating the position of the cord positioner rather than by touching the first cord;

removing the first cord from the body;

attaching a second cord of a second corded instrument to a cord positioner attachment;

attaching the cord positioner attachment to the body;

positioning the second cord away from a procedure being performed by the technician by manipulating the position of the cord positioner rather than by touching the second cord;

removing the cord positioner attachment from the body; and leaving the cord positioner attachment attached to the second cord; and wherein the step of attaching the cord positioner attachment to the body is characterized by inserting a head of the cord positioner attachment into a channel of the body.

2. The method of claim 1 further comprising the step of aligning the cord positioner attachment when attaching the cord positioner attachment using alignment arms and guides that are spaced from either side of the head.

3. The method of claim 1 wherein the head is substantially cylindrical, with a neck connected to an attachment body of the cord positioner attachment;
and wherein a diameter of the channel is substantially the same as a diameter of the head.

4. A method for positioning a cord of a corded instrument, comprising the steps of:
   securing a band of a cord positioner to a wrist of a technician, said band including a body;
   attaching a first cord of a first corded instrument to the body;
   positioning the first cord away from a procedure being performed by the technician by manipulating the position of the cord positioner rather than by touching the first cord;
   removing the first cord from the body;
   attaching a second cord of a second corded instrument to a cord positioner attachment;
   attaching the cord positioner attachment to the body;
   positioning the second cord away from a procedure being performed by the technician by manipulating the position of the cord positioner rather than by touching the second cord; and
   wherein the step of attaching the cord positioner attachment to the body is characterized by bringing a magnetic portion of the base into close proximity to a permanent magnet that is fixed to the cord positioner attachment such that a magnetic attraction attaches the cord positioner attachment to the body.

5. The method of claim 4 wherein the magnetic portion is at least partially surrounded by a relief; and the permanent magnet, once magnetically attached in a desired orientation, will not rotate within the relief.

* * * * *